United States Patent [19]
Doherty

[11] Patent Number: 5,535,754
[45] Date of Patent: Jul. 16, 1996

[54] ENDOSCOPIC BIOPSY FORCEPS - DISPOSABLE

[76] Inventor: Thomas E. Doherty, 7 Carriage La., Setauket, N.Y. 11733

[21] Appl. No.: 205,553

[22] Filed: Mar. 4, 1994

[51] Int. Cl.$^6$ .................................................. A61B 17/28
[52] U.S. Cl. ........................... 128/751; 606/205; 606/208
[58] Field of Search .................................... 606/205, 206, 606/207, 208; 128/751

[56] References Cited

U.S. PATENT DOCUMENTS

| | | | |
|---|---|---|---|
| 3,895,636 | 7/1975 | Schmidt | 606/205 |
| 4,887,612 | 12/1989 | Esser et al. | 128/751 |
| 5,238,002 | 8/1993 | Derlin et al. | 128/751 |
| 5,282,806 | 2/1994 | Haber et al. | 606/139 |

Primary Examiner—Michael H. Thaler
Assistant Examiner—Patrick W. Rasche

[57] ABSTRACT

An endoscopic biopsy forceps mechanism encompassing a device of integrally designed parts for selectively opening and closing the biopsy forceps cutting jaws of the forceps and dramatically reduce the number of individual parts in the entire device thereby rendering a forcep mechanism of a more simplified construction, more reliable in operation and concurrently reduce the manufacturing and assembly costs.

7 Claims, 5 Drawing Sheets

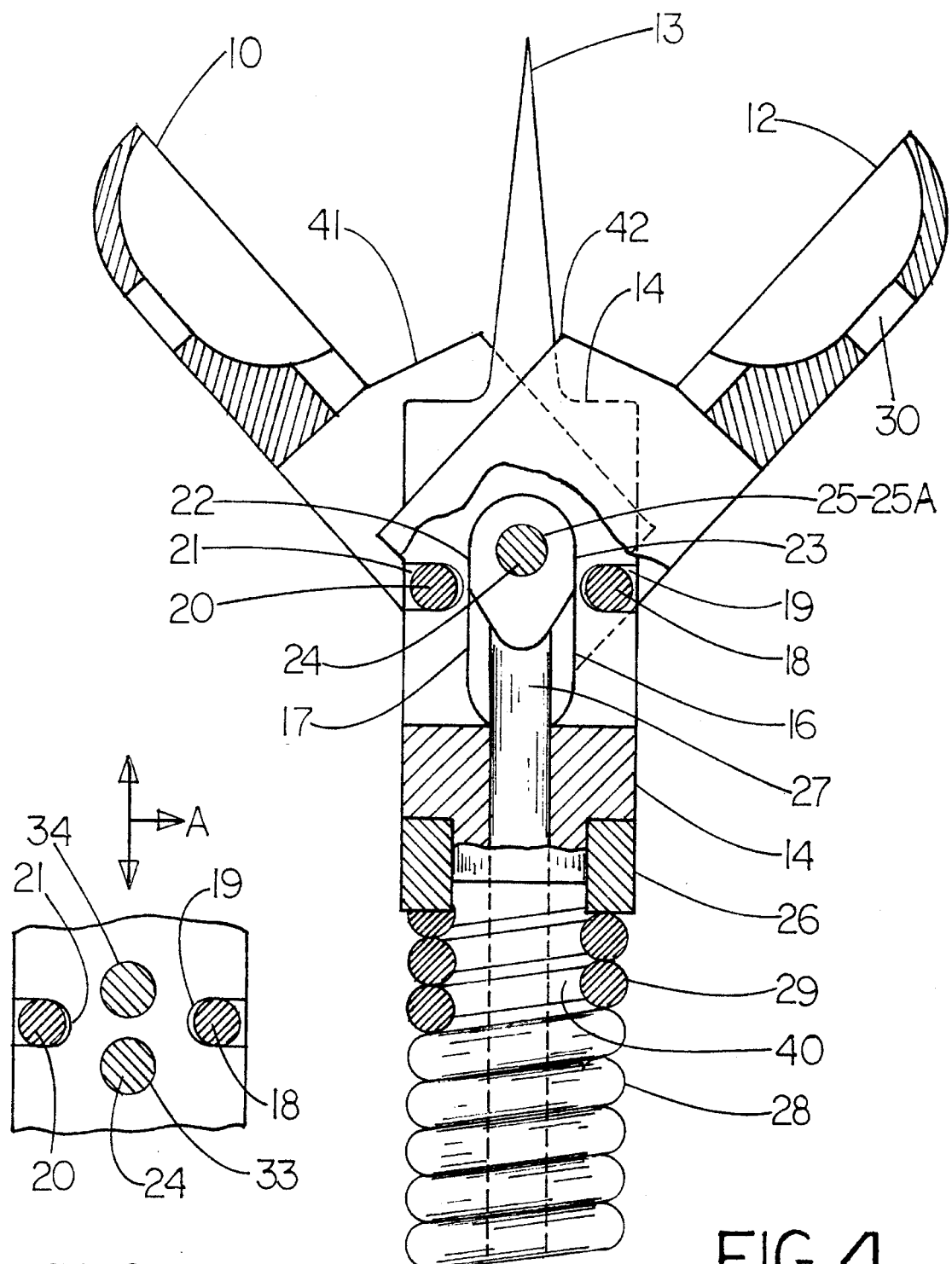

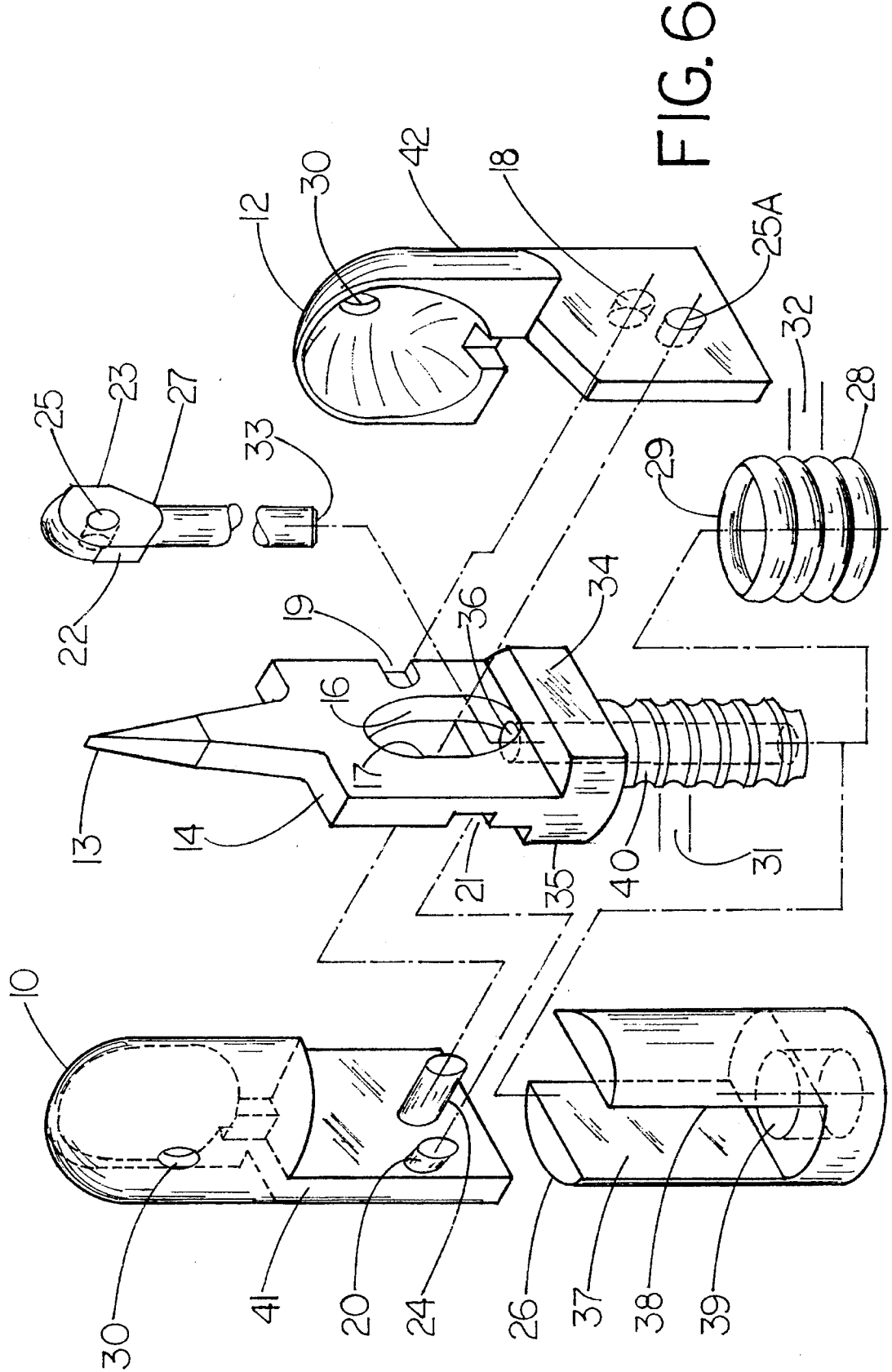

ENDOSCOPIC BIOPSY FORCEPS - DISPOSABLE

BACKGROUND OF THE INVENTION

1. Field of the Invention

The present invention relates to an endoscopic biopsy forceps. It is a new and novel means of actuating the forceps as they are selectively articulated in the opening and closing actions of the cutting procedure. The integral construction is such, that it provides a surgical instrument of the most simplified construction thereby reducing the complexity and cost of the individual parts and concurrently reduces the manual labor involved in the assembly processes.

Many and varied designs of biopsy forceps are currently employed in the medical field within the endoscopic procedure concept. They are, in general, mostly of a more complicated nature, incorporating a multiplicity of highly precise and delicate parts requiring labor intense assembly procedures. This invention is specifically created to reduce the number of parts employed in the device and to greatly reduce the time and cost involved in the assembly. It is designed as a single use throwaway item. It eliminates the need for resterilization that is presently found in the prior art with reuseable biopsy forceps. In recent years it has been found that resterilization, whether by chemical means or by the use of an autoclave, has not always been adequately performed for the reuse of the instruments in a subsequent procedure. This can cause considerable dangerous risks to patients of potentially severe infections and sometimes life threatening diseases such as the AIDS virus. Cross contamination can possibly subject a medical facility and/or staff to costly and prolonged litigation caused by the use of poorly sterilized and contaminated biopsy forceps devices. Furthermore, resterilizing a biopsy forceps in the rigorous environment of an autoclave can seriously impair the precise and delicate parts of the forcep causing a malfunction or breakdown in subsequent endoscopic procedures.

Recognizing the complexity and the multiplicity of parts currently employed in the biopsy forceps designed for use in endoscopic procedures that meet with the approval of the Federal Drug Administration and the medical profession this invention precludes the use of the multiplicity of components that is evident in the prior art. By its integrated design it reduces the number of parts to the barest minimum and concurrently provides an instrument of the highest quality at the lowest possible cost. It gives the medical technician a more reliable device due to the manner in which the mechanical components are manufactured and assembled. The assembly process of this invention precludes the use of separate pivot pins, pivot pin holes, screws, shims, rivets and the critical riveting operations, soldering, toggle links and cam tracks. The elimination of the multiplicity of manufactured parts and the tedious assembly procedures found in the prior art reduces the unit cost and renders a more reliable device than that which is currently available.

2. Discussion of the Prior Art

The current state of the art technology found in the field of endoscopic biopsy forceps is exemplified in the Esser-Doherty U.S. Pat. No. 4,887,612. In this concept the usual types of pivot pins and screws normally used to open and close the forceps are still evident. The toggle links, usually found in the prior art have been replaced with a cam track cut in the shank portion of the forcep to articulate the action of the device. It should be noted that the cam tracks, while effectively actuating the forceps from the open to closed position, diminish the cross sectional structural strength of the shank portion of the forcep. Conversely, this invention, by the embodiment of its integral design, dramatically increases the cross sectional structural strength of the shank portion of of the forceps by the elimination of cam tracks and holes that are used for pins and screws.

The following list of patents, which are cited in the Esser-Doherty U.S. Pat. No. 4,887,612 mentioned above, are considered to be representative of the current state of the art technology.

Komiya U.S. Pat. No. 4,038,987

Blake, III, U.S. Pat. No. 4,662,374

Rich, U.S. Pat. No. 4,572,185

Walter et al, U.S. Pat. No. 4,171,701

Additional designs of biopsy forceps, all of which use a multiplicity of complex parts and pivot points, linkages, toggle arrangements and soldering operations are respectively shown in Komiya U.S. Pat. No. 3,840,003; Hayashi U.S. Pat. No. 4,669,471; Maslamka U.S. Pat. No. 4,646,751; and Schmidt U.S. Pat. No. 3,895,636. It can be seen from what is disclosed therein that the multiplicity of complex parts, toggle links, linkage systems, screws, and rivets all tend to add to the manufacture of, and assembly, of extremely delicate components requiring a high degree of manual labor thereby concurrently escalating the unit cost of the devices. The high cost of these devices preempts their sale as a single use, throwaway instrument.

SUMMARY OF THE INVENTION

The new and novel feature of this invention is such that it is composed of parts that are integral in their design and manufacture. For example, in the prior art, separate and individual pivot pins are employed to articulate the motion of the forceps. These parts, as well as others have been eliminated by the embodiment of circular projections that are manufactured as an integral part of the forcep. Accordingly, the structural integrity of the forcep jaw has been dramatically strengthened by the elimination of cutting cam tracks, drilling holes for screws, pins and the like. This novel approach, of using an integral design of parts for forceps used in the field of endoscopy has effectively reduced the multiplicity of individual components to the barest minimum. This novel technique, of employing an integral design concept in the field of endoscopic forceps has extensively reduced the production costs of the devices and concurrently eliminates numerous assembly procedures of a tedious manual nature evident in the prior art. The production costs are reduced to such an extent it enables the forceps devices to be economically employed and then discarded after a single use. In essence, it causes the devices to become known as a low cost single use throwaway endoscopic biopsy forceps. It eliminates the necessity of resterilization and completely obviates the danger of cross infection to a patient by the secondary use of a reuseable biopsy forceps.

In achieving the foregoing objective, this invention for an endoscopic biopsy forceps device, encompasses a novel arrangement of consolidating the mechanical components so as to accomplish a one piece design, so to speak.

The circular projections of the forceps extend sufficiently outward from the shank portion of the forceps so as to engage a guide provided in the shank portion of the center stem, thereby effecting an arrangement for imparting an articulating action to the forceps. Another circular projection extending from the shank portion of the forceps is engaged in the orifice of a reciprocating drive wire which in turn is attached at the distal end to the operating handle of the forceps. The reciprocating drive wire is slidably supported and guided by the center stem in order to provide the correct alignment with the circular projections of the forceps.

The reciprocating movement of the drive wire, causes the forceps to rotate about the circular projections from the open to the closed position. In the prior art, the trocar or spike used for piercing the tissue in a body cavity, is fabricated as a separate part, which, is delicate in nature and tedious to assemble manually. Accordingly, in this invention the trocar or spike is an integral part of the center stem, thereby, providing an increase in the strength of the part and concurrently eliminating the tedious assembly procedure evident in the prior art.

BRIEF DESCRIPTION OF THE DRAWINGS

Contained in the following detailed description of the embodiments of the invention are illustrations of the specified construction for an endoscopic biopsy forceps device using the technique of combining components so as to reduce the multiplicity of parts evident in the prior art.

FIG. 4 shows a longitudinal cross section of the forceps in the open position. It illustrates the horizontal displacement of the circular projections with the drive wire.

FIG. 5 is an illustration of the interaction of the circular projections and the drive wire as the forceps oscillate from the open to closed position.

FIG. 6 is an exploded perspective view of the forceps assembly illustrating the relationship of the operating components to one another. It shows quite clearly the embodiment of the invention and the manner in which the multiplicity of parts has been dramatically reduced when compared to the complex designs of the prior art.

DETAILED DESCRIPTION OF THE DRAWINGS

Referring now in specific detail to the drawings illustrated in FIG. 1 through FIG. 6 in which like reference numbers identify similar or identical components.

Figure 1:
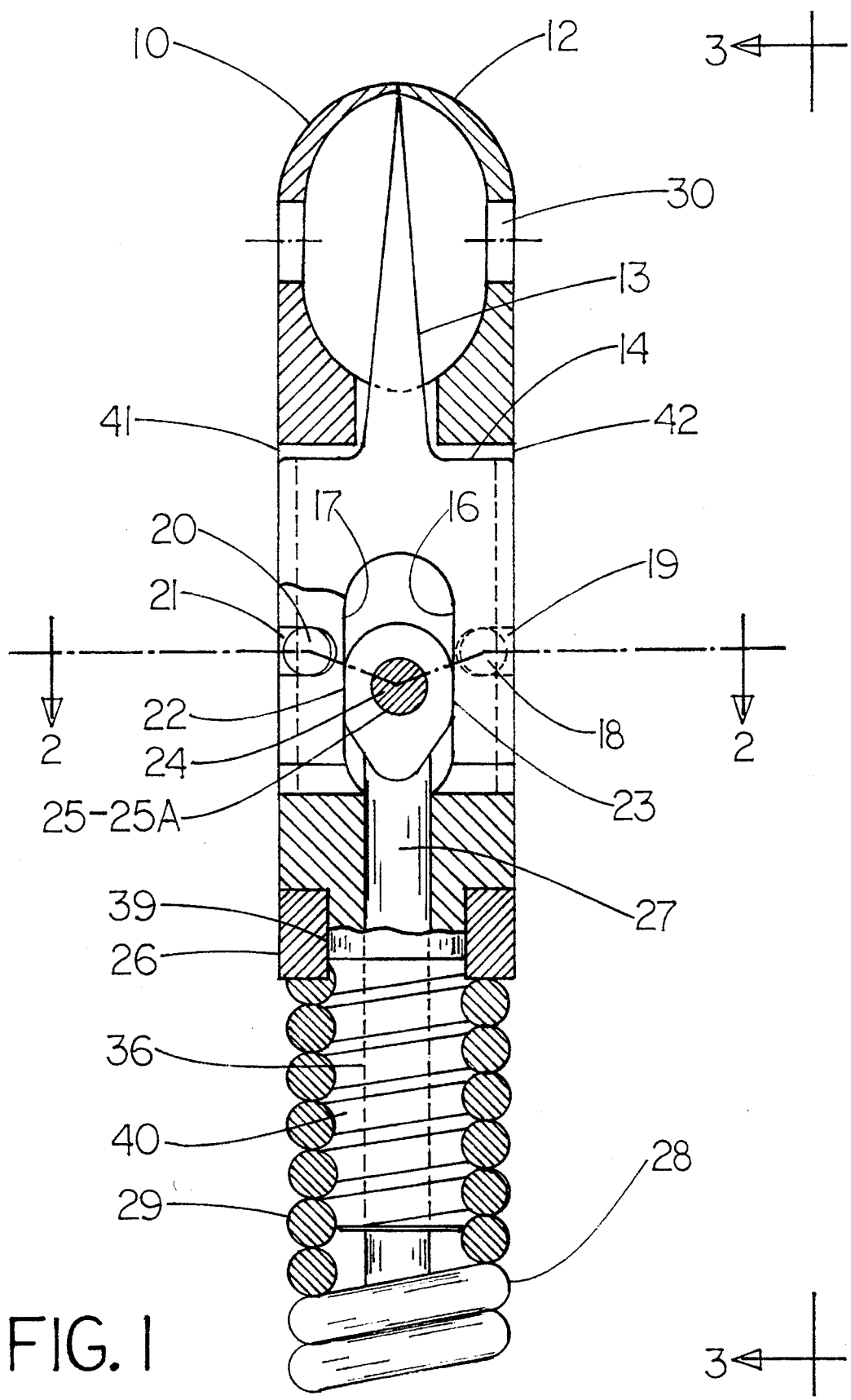
FIG. 1 is a longitudinal cross sectional view of the functional end of the biopsy forceps illustrating the forceps in the closed position. It should be specified here that the longitudinal overall axial length of the forceps is shorter then that which can be found in the prior art thereby allowing the endoscope to bend in a smaller radii.

FIG. 1 illustrates the forceps jaws 10 and 12 in the closed position. The jaw 10 extends to one end of the shank portion 41 while the circular projection 20, about which the jaw 10 oscillates, is an integral part of the shank portion 41 at the other end. Similarly, the jaw 12 extends to one end of the shank portion 42 while the circular projection 18, about which the jaw 12 oscillates, is an integral part of the shank portion 42 at the other end. The integral construction of the shank portions 41 and 42 and the circular projections 20 and 18 will be seen more clearly when referring to FIG. 2. The circular projection 20 is slideably inserted in the guide 21 and the circular projection 18 is slideably inserted in the guide 19. The guides 21 and 19 are an integral part of the center stem 14. The trocar or spike 13 is also an integral part of the center stem 14. The circular projection 24 which is an integral part of the jaw 10 is permitted to oscillate in a precise relationship with the orifice 25 of the drive wire 27 and the orifice 25A of the forcep jaw 12. The drive wire 27 which is connected at the distal or handle end of the instrument is slideably mounted in a reciprocating manner with the opening 36 in the main stem 14. The surfaces 22 and 23 of the drive wire 27 interface in a slideable precise relationship with the surfaces 16 and 17 of the center stem 14. The threaded portion 40 is an integral part of the center stem 14 and slips through the opening 39 of the yoke 26. The outer flexible metal sheath 29 is engaged with the thread 40 of the center stem 14 and clamps the yoke 26 in a fixed relationship with the center stem. This relationship will be discussed in greater detail in FIG. 6.

Figure 2:
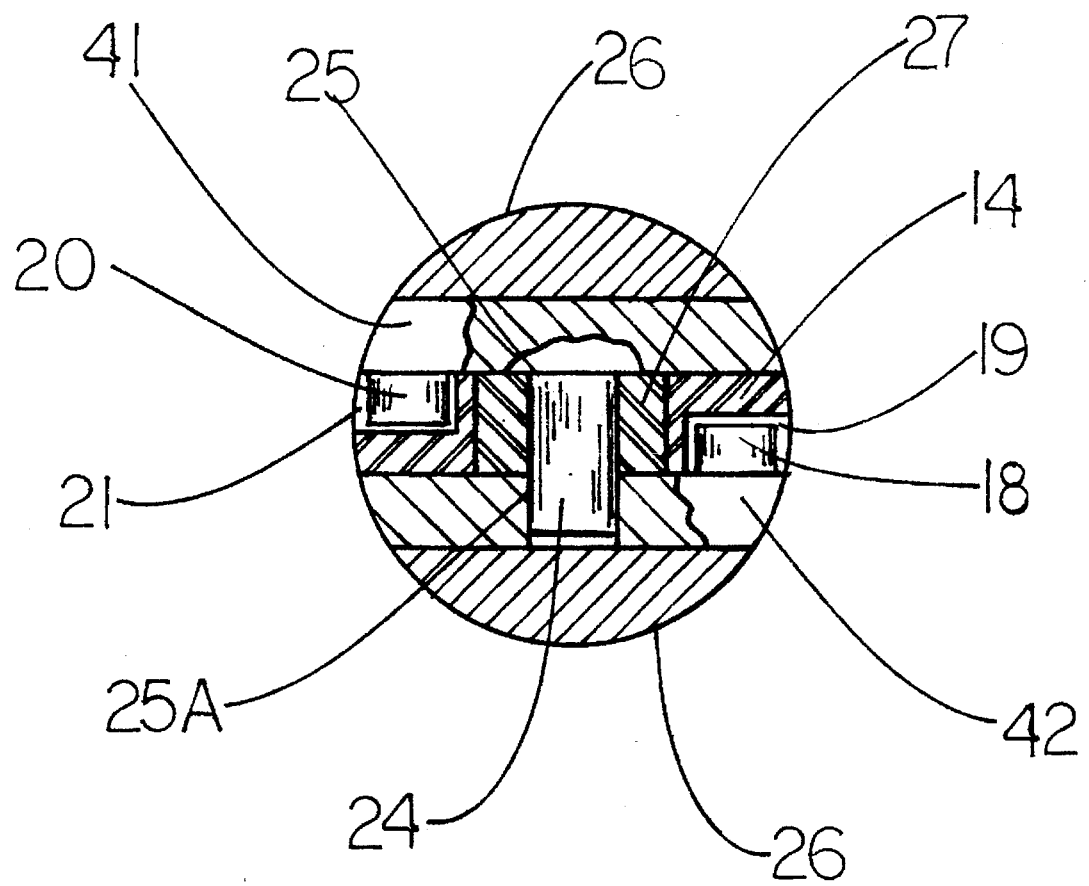
FIG. 2 is a cross sectional view taken along the Line 2—2 of FIG. 1. Illustrated here is the embodiment of the integral design and the alignment of the forceps with the drive wire and the center stem.

FIG. 2 is a cross sectional view taken along the line 2—2 of FIG. 1. It illustrates the relationship of the components in a transverse position, and shows more clearly the integral construction of the parts. The yoke 26 encapsulates the components of the forceps in a close fitting, laterally slideable relationship and prevents any transverse movement of the shank portions 41 and 42. FIG. 2 also shows, quite dramatically, the manner in which the numerous individual parts embodied in the prior art have been eliminated by the novel and profound construction described in this integral design concept. The employment of integral circular projections in place of separate and individual pivot pins, and the like, enhances the reliability of the instrument.

Figure 3:
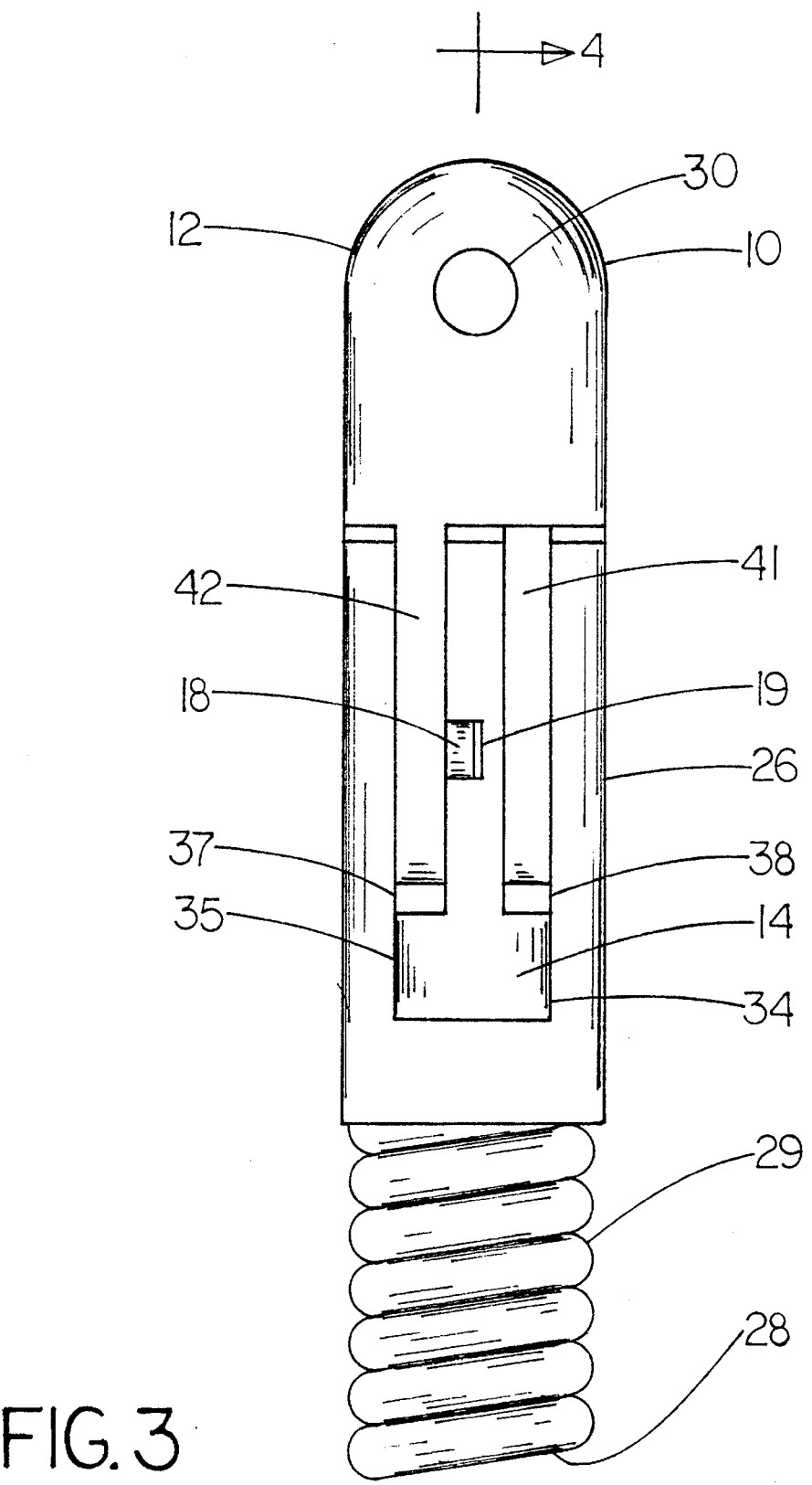
FIG. 3 illustrates a side elevation of the forceps taken from the view 3—3 of FIG. 1. It shows the manner in which the circular projections, an integral part of the forceps, are positioned in the center stem in order to impart an oscillating motion to the forceps.

FIG. 3 is a side elevation taken along the lines 3—3 of FIG. 1. It illustrates the vertical and horizontal orientation of the shank portions 41 and 42 and their respective forceps jaws 10 and 12, with the center stem 14 and the yoke 26. The flat surfaces 34 and 35 of the center stem interfaces respectively with the corresponding flat surfaces 38 and 37 of the yoke 26, thereby, preventing any axial rotation between the center stem 14 and the yoke 26. In essence, the shank portions 41 and 42 of the forceps are precisely contained between the flat surfaces of the center stem 14 and the yoke 26, therefore providing excellent guidance during the articulation of the forceps device and in particular when the forceps are in the open position. Also, as shown in this view, the yoke 26 retains the circular projection 18 in the correct operational attitude with the guide 19 of the center stem. This condition also exists on the opposite side of the shank portions 41 and 42 where the circular projection 20 is retained in the guide 21.

Referring now to FIG. 4. FIG. 4 is a longitudinal cross-sectional view taken along the line 4—4 of FIG. 3. It demonstrates the forceps jaws 10 and 12 in the open position and, illustrates the position of the operating components to attain this position. Due to the reciprocal action shown by the arrow "A", (FIG. 5) it can be seen that the circular projection 24, which is an integral part of the shank portion oscillates in the orifice 25 of the drive wire 27 as well as the orifice 25A which is located in the shank portion 42. Also, it can be seen more clearly the manner in which the circular projections 18 and 20 are positioned in their respective guides 19 and 21 of the center stem 14.

Shown in FIG. 5 is the relative position of the circular projection 24 as it reciprocates in the direction of the arrow "A" by the action of the drive wire 27. When the forceps jaws are in the closed position the circular projection 24 is in the location shown at 33. And, when the circular projection 24 is in the location at 34 the forceps jaws 10 and 12 are in the open position. When this reciprocating action takes place the circular projections 20 and 18 are permitted to move laterally in the guides 19 and 21 of the center stem 14. This is a new and novel embodiment in this invention that cannot be found in the prior art where fixed and rigid pivot pins and screws are employed.

Illustrated in FIG. 6 is an exploded perspective view of the concept of integral design employed in the construction of this biopsy forceps. The distal end 33 of the drive wire 27 is inserted through the orifice 36 of the center stem 14 so that the faces 22 and 23 of the drive wire 27 are in a slideably precise relationship with the faces 16 and 17 of the center stem 14. When assembling the shank portion 41 with the stem 14, the circular projection 24 passes through the orifice 25 of the drive wire 27 and enters the orifice 25A of the shank portion 42. Simultaneously, the circular projection 20 enters the guide 21 of the center stem 14. When assembling the shank portion 42 to the stem 14 the circular projection 24 enters the orifice 25A of the shank portion 42. Simultaneously, the circular projection 18 enters the guide 19 of the stem 14. With the drive wire 27, and the shank portions 41 and 42 assembled to the center stem 14, the yoke 26 is slipped over the distal end 33 of the drive wire 27 and placed in position with the center stem 14 so that the surfaces 37 and 38 interface with the surfaces 34 and 35 of the center stem 14. The orifice 39 in the yoke 26 permits the threaded portion 40, which is an integral part of the stem 14, to extend beyond the yoke 26 and provides a threaded shank to which the flexible metal sheath 29 can be affixed. The metal sheath, commonly used in the field of endoscopic forceps, is assembled by placing the leading edge of the sheath 29 over the distal end 33 of the drive wire 27 and threading it over the threaded portion 40 of the inside center stem 14. The inside contour of the sheath 29 is similar in configuration to the outside contour of the threaded portion 40 of the stem 14. But, the axial pitch 31 of the thread 40 is perceptively greater than the axial pitch 32 of the metal sheath 29. This premeditated design feature, employs the latent axial spring tension of the metal sheath and automatically provides a lockwasher effect in the retention of the sheath 29 to the center stem 14. As can be seen more clearly in FIG. 1 and FIG. 4 the entire forceps assembly is locked together in a positive and dependable manner. It is noteworthy here, to review the configuration of the shank portions 41 and 42 and the manner in which the structural integrity of the forceps has been dramatically improved by the adaptation of the integral design concept. The distal end 28 of the sheath 29 is attached to the operating handle not shown in these illustrations, but common in the endoscopic biopsy forceps field. The orifice 30 in the jaws 10 and 12 is a vent to avoid air entrapment when removing a body tissue with the jaws in the closed position.

For those skilled in the art, it becomes readily apparent that the embodiment presented in the foregoing is a new and novel inventive approach of employing an appreciably fewer number of parts, of a less complicated nature, than any of the forceps devices currently found in the prior art, The concept of employing an integral design increases the structural strength of the individual components and renders the entire forceps device less expensive to manufacture. Concurrently, the assembly process has been appreciably accelerated thereby further adding to the reduction in cost.

Other advantages that can be offered by this inventive construction is contained in the following:

(a) the overall longitudinal axial dimension of the forceps described herein, is of a lesser distance in comparison with those in the prior art. This feature permits the endoscope to bend in a smaller radius than that which is presently possible in endoscopic biopsy procedures.

(b) the trocar or spike, which, in the prior art has traditionally been a separate part has now been made an integral part of the center stem. This embodiment has a dramatic positive effect in the strength of this component (c) when closing the forceps jaws, the added strength of the spike controls the tissue specimen in a more rigid manner for the cutting action of the forceps.

(d) using the axial latent energy of the outer metal sheath to lock the forceps assembly in a lockwasher fashion is a new and inventive approach in this field.

(e) the circular projections, an integral part of the shank portions of the forceps, are permitted to float in their respective guides during the articulation of the forceps jaws.

(f) the simplicity of the integral design in this invention, provides a substantially lower manufacturing cost. It gives the technician an exceptionally high degree of reliability and confidence when performing endoscopic biopsy procedures.

(g) when compared to the prior art, the overall assembly requirements for this invention has been dramatically reduced. The errors generally caused by the human element factor have been omitted by the embodiment of an integral design. The employment of separate pins, screws, shims, riveting, linkages, soldering and cam tracks has been eliminated. These tedious, delicate procedures have been omitted.

(h) the reduction in the number of components and the lower assembly costs renders this forceps device marketable as a single use, throwaway instrument at a low price. It eliminates all danger to a patient from contamination when a poorly sterilized reuseable forceps is employed.

What has been described and illustrated herein, is considered to be the preferred embodiments of the invention. It will, of course, be understood that various alterations and changes in the form of detail could readily be made without departing from the spirit of the invention. Therefore, it is the intention that the invention be not limited to the exact form than the whole of the invention herein disclosed and as hereinafter claimed.

What is claimed is:

1. A biopsy forceps device which is adapted to be inserted through an endoscope into a body cavity for the removal of a polyp or body tissue therefrom; said device comprising a flexible metal, tight wound wire sheath having proximal and distal ends and an orifice therethrough; a center stem with first and second ends coupled to said sheath, the first end of said center stem having an integrally formed projection with external threads for attachment to the distal end of said sheath, the second end of said center stem having a trocar extending therefrom, the center stem having two perpendicular orifices, the first orifice extending through the integrally formed projection and into the second orifice, two elongated guides integrally formed on said center stem and located on either side of said second orifice; a drive wire extending coaxially within the metal sheath for a reciprocating movement within the sheath and having a precise slidable relationship with the center stem, said drive wire having a distal end and an orifice near the distal end, said distal end of the drive wire positioned within the second orifice of the center stem; a pair of forceps, each having a shank portion with first and second ends, said shank portions having integral circular projections formed near the first ends and operating jaws extending from the second ends end; the integrally formed circular projections of the forceps engaging the elongated guides of the center stem as well as the orifice of the drive wire; with the circular projections engaged in the center stem and the drive wire, the axial reciprocating motion of the drive wire relative to the center stem and the metal sheath articulates the forceps into respective opening and closing movements of the cutting action of the forceps jaws.

2. A forceps device as claimed in claim 1, and further comprising: a housing with an orifice extending therethrough and a transverse opening, said housing locking said forceps into a pivoting relationship with said center stem.

3. A forceps device as claimed in claim 1, wherein said projections of said forceps slidably engaging said elongated guides.

4. A forceps device as claimed in claim 3, wherein said projections of said forceps are laterally disposed in said elongated guides by the reciprocating movement of said drive wire.

5. A forceps device as claimed in claim 1, wherein the distal end of the metal sheath is threaded onto the integrally formed projection of the center stem.

6. A forceps device as claimed in claim 5, wherein said distal end of the metal sheath adapts the latent axial tension of said sheath in securing a reliable connection.

7. A forceps device as claimed in claim 1, wherein the trocar is an integrally formed upward extension of the center stem.

* * * * *